United States Patent [19]
Cox et al.

[11] Patent Number: 5,829,442
[45] Date of Patent: Nov. 3, 1998

[54] ANTIMICROBIAL CONTAINING SOLVENTLESS HOT MELT ADHESIVE COMPOSITION

[75] Inventors: David D. Cox, Woodbury; Robert E. Lund, Eagan; Leland W. Annett, Baytown, all of Minn.

[73] Assignee: Medical Concepts Development, Inc., St. Paul, Minn.

[21] Appl. No.: 662,850

[22] Filed: Jun. 12, 1996

[51] Int. Cl.⁶ ..................................................... A61B 19/00
[52] U.S. Cl. ........................................... 128/849; 128/852
[58] Field of Search .................................... 524/204, 238, 524/240, 262, 501, 502; 602/41, 56; 128/849–856

[56] References Cited

U.S. PATENT DOCUMENTS

| | | | |
|---|---|---|---|
| 2,137,169 | 11/1938 | Levey | 167/84 |
| 3,249,109 | 5/1966 | Maeth et al. | 128/268 |
| 3,632,740 | 1/1972 | Robinson et al. | 424/28 |
| 3,734,097 | 5/1973 | Zaffaroni | 128/268 |
| 3,769,071 | 10/1973 | Trancik | 117/122 |
| 3,896,789 | 7/1975 | Trancik | 128/2 R |
| 4,073,291 | 2/1978 | Marvel et al. | 128/155 |
| 4,310,509 | 1/1982 | Berglund et al. | 424/28 |
| 4,323,557 | 4/1982 | Rosso et al. | 424/28 |
| 4,750,482 | 6/1988 | Sieverding | 602/56 |
| 5,069,907 | 12/1991 | Mixon et al. | 424/445 |
| 5,500,470 | 3/1996 | Mirle | 524/204 |

FOREIGN PATENT DOCUMENTS 2 271 719  4/1994  United Kingdom.

*Primary Examiner*—Michael A. Brown
*Attorney, Agent, or Firm*—Nawrocki, Rooney & Sivertson, P.A.

[57] ABSTRACT

An adhesive composition having dispersed therein a broad spectrum antimicrobial agent for use in medical applications, such as an adhesive for surgical drapes, wound dressings and tapes. The adhesive is composed of acrylic polymers, tackifiers and a preferred antimicrobial agent, diiodomethyl-p-tolylsulfone. The adhesive composition is essentially solventless and capable of application in a hot melt process while maintaining stability at elevated temperatures in the range of 275° F. to 350° F., which not only allows hot melt application, but allows for ethylene oxide sterilization under heat stress.

19 Claims, 1 Drawing Sheet

ANTIMICROBIAL CONTAINING SOLVENTLESS HOT MELT ADHESIVE COMPOSITION

TECHNICAL FIELD

The present invention relates to a medical grade, antimicrobial-containing adhesive particularly suited for use in skin contact applications, such as with surgical drapes, tapes and wound dressings. More particularly, the adhesive compound is essentially a 100% solids or essentially solventless hot melt adhesive incorporating an acrylic polymer in conjunction with diiodomethyl-p-tolylsulfone as an antimicrobial agent.

BACKGROUND OF THE INVENTION

It is recognized that numerous pathogens are present on human skin. Therefore, in a hospital environment, it is generally desired that the growth of disease-producing microorganisms be inhibited, and preferably that these microorganisms be destroyed so as to control patient infection and encourage wound healing. Under most circumstances, the bacteria of normal skin cannot cause wound infections, but in the presence of foreign materials or open wounds, the pathogenic potential of these bacteria appears to be considerably enhanced. Furthermore, the likelihood of bacterial contamination is at a peak immediately preceding, during, and following surgical procedures. Accordingly, to prevent contamination, it is imperative that the skin be effectively disinfected before a surgical incision is made and during the entire surgical procedure.

In response to such concerns, many topical antimicrobial agents have been developed. These agents typically are in the form of preoperative skin preps, surgical scrub tissues, washes, wound cleaners, lotions and ointments. A recognized limitation to such topical applications are a short effective delivery time. Microorganisms that may have survived the initial application of such a topical antimicrobial agent can act as a seed, causing the pathogen population in some instances to regenerate or rise to their initial levels. Thus, continuous application of an antimicrobial agent to the site is recognized as a means of inhibiting this increase in population.

It has been recognized that a continuous or longer lasting antimicrobial effect may be achieved by incorporating the antimicrobial agent into an adhesive layer or into a surgical incise drape material itself.

Berglund et al. (U.S. Pat. No. 4,310,509) disclose that it is known to incorporate biologically active agents into adhesive layers on a substrate to provide continuous application of such agent to the body. Disclosed examples of known adhesives containing antimicrobial agents include U.S. Pat. No. 2,137,169, wherein phenol, thymol, methanol, etc. are added to a starch adhesive; U.S. Pat. No. 3,249,109 where benzocaine was added to a tacky gelatin; U.S. Pat. No. 3,632,740 where a corticosteroid is added to an adhesive; U.S. Pat. No. 3,734,097 where a microencapsulated anti-neoplastic agent is added to an adhesive; U.S. Pat. No. 4,073,291 where Tretinoin is added to an adhesive; U.S. Pat. No. 3,769,071 where 5-fluorouracil is incorporated into an adhesive; and U.S. Pat. No. 3,896,789 where retinoic acid is incorporated into a pressure-sensitive adhesive tape. Berglund et al. further teach that the prior art attempts to include an antimicrobial agent in an adhesive did not include the use of a broad spectrum antimicrobial because such adhesives had been frustrated by uncontrollable release of the agent with accompanying skin irritation in some patients, along with failure to obtain sufficient antimicrobial activity.

Berglund et al. disclose a pressure sensitive adhesive composition which contains chlorhexidene, polyvinylpyrrolidone iodine or iodine which is applied onto a polymer sheet material, such as polyethylene or polyurethane, for use as a surgical drape. The disclosed drape is applied to the skin with the adhesive side contacting the skin so that the antimicrobial agent can be released from the adhesive to the wound area prior to and during incision. The process for making the adhesive disclosed by Berglund et al. involves forming an emulsifiable concentrate or an organic solution concentrate of a broad spectrum antimicrobial agent and mixing it into an adhesive, such that the broad spectrum antimicrobial is homogeneously dispersed as a separate phase throughout the adhesive medium. The homogenous dispersion is then spread or coated to a substantially uniform layer followed by drying of the wet layer in order to remove the solvents.

Rosso et al. (U.S. Pat. No. 4,323,557) disclose a drape incorporating a pressure sensitive adhesive utilizing n-vinylpyrrolidione residues in the polymer backbone. Iodine is complexed with these residues to provide an antimicrobial effect. Rosso et al. espouse the stability of the adhesive composition over the prior art compositions. By stable, Rosso et al. asserts that a composition coating of 11 grains per 24 sq. in. which is attached to a polyethylene sheet can be exposed to a temperature of 120° F. and a relative humidity of 9% for two weeks or to a dose of 2.5 megarads of gamma irradiation without substantial alteration of the physical appearance or of the chemical activity as tested by the starch test and microbiological activity as tested by the zone inhibition assay. The disclosure of Rosso et al. is incorporated herein by reference.

The process for forming the adhesive composition disclosed by Rosso et al. involves forming a pressure-sensitive adhesive and mixing into it an antimicrobial treating solution comprising iodine, an iodide, and a solvent. The resulting composition preferably contains n-vinylpyrrolidone in the backbone of the pressure-sensitive adhesive which serves to complex the iodine. Rosso et al. disclose that the composition may be either attached directly onto a flexible backing substrate or formed onto a release liner for later use. Once applied, the solvents are then evaporated by means known to the art, whereby an adhesive film is formed which is useable in or on tapes, drapes and other medical devices.

Mixon et al. (U.S. Pat. No. 5,069,907) disclose a surgical drape having incorporated therein a broad spectrum antimicrobial agent. The drape comprises a synthetic polymeric film or fabric having incorporated therethrough an amount of antimicrobial agent. The drape may optionally have an adhesive layer attached to one of its external surfaces, wherein the adhesive layer can have dispersed therethrough an antimicrobial agent. The preferred antimicrobial agent used is 5-chloro-2-(2,4-dichlorophenoxy)phenol. Suitable adhesives utilized include polyacrylate adhesives.

Mixon et al. disclose a large number of antimicrobial agents which were contemplated for use with the disclosed composition. These include metal salts, typical antibiotics, antibacterial agents such as chlorhexidine and its salts, quaternary ammonium compounds, iodophors such as povidone iodine, acridine compounds, biguanidine compounds, and a preferred antimicrobial agent 5-chloro-2-(2,4-dichlorophenoxy)phenol. Mixon et al. further disclose that these same antimicrobial agents, which they propose to utilize within the polymer composition for their surgical drape, can also be utilized in an adhesive composition. Mixon et al. further state that the antimicrobial agent can be directly applied to the surgical drape in solution as an aqueous dispersion, as a hot melt, or by a transfer process using known techniques, such as knife, roller-coating, or curtain-coating methods. The transfer process is disclosed as particularly preferred. In a transfer process, the adhesive emulsion, including water or a different solvent, optionally containing an antimicrobial agent, is spread onto a sheet of release paper and dried to remove the water or solvent. The surgical drape is then brought into contact with the adhesive and calendared to insure that the adhesive adheres to the drape. The surgical drape will then generally include a release sheet covering the adhesive, and the release sheet on which the adhesive is deposited can be used for that purpose, or that release sheet can be removed and replaced with another release sheet. In embodiments where the adhesive contains an antimicrobial agent, the mixture of adhesive and antimicrobial agent is dried after coating on the release sheet, and the antimicrobial agent remains dispersed in the adhesive.

Generally, presently known antimicrobial agents are limited in their ability to withstand heat during processing. The lack of heat stability of n-vinyl pyrrolodione iodine has limited the ability for drapes having this antimicrobial agent from being ethylene oxide sterilized under heat stress. Further, many of the antimicrobial compounds cannot be radiation sterilized. Thus, each prior art reference teaches that it is preferred to apply the antimicrobial adhesive in conjunction with a solvent followed by subsequent evaporation of the solvent.

Accordingly, the need exists for an adhesive composition having an antimicrobial agent dispersed therethrough which is heat stable and solventless. Such composition would eliminate the need for use of solvents with their potential environmental effects and would eliminate the need for removing such solvent from the adhesive after application to the drapes. Further, the heat stability would allow the solventless adhesive to be applied in a hot melt process, while also allowing for ethylene oxide sterilization under heat stress or radiation sterilization.

SUMMARY OF THE INVENTION

The present invention is an adhesive composition having a broad spectrum antimicrobial agent dispersed therethrough. The adhesive composition is an essentially solventless composition (100% solids), which is heat stable so that it may be applied in a hot melt process, while also being capable of ethylene oxide sterilization under heat stress without loss of effectiveness of the antimicrobial agent. Specifically, the adhesive is for skin-contact applications, for example, surgical drapes, tapes and wound dressings. The antimicrobial agent utilized is diiodomethyl-p-tolylsulfone with a preferred concentration of antimicrobial agents in the adhesive of about 0.1% to about 2% loading by weight.

The antimicrobial agent is homogeneously dispersed through the adhesive layer. Active antimicrobial molecules continually disassociate from the surface or leach out of the adhesive matrix over time, delivering biocidal activity at a distance from the adhesive surface. Applicants have conclusively demonstrated this property by zone of inhibition tests on a wide variety of infectious organisms. These tests conclusively showed that microbes were inhibited at a distance from the sample.

Adhesive compositions can incorporate acrylic or rubber based polymers to form the hot melt adhesive. A preferred composition includes a mixture of two acrylic polymers, one of which is a low molecular weight solid acrylic polymer, the other a medium molecular weight solid acrylic polymer, which are both designed for hot melt pressure-sensitive adhesive applications. A low molecular weight solid acrylic polymer is available from Schenectady International, Inc. as Product No. HRJ-4326, and a medium molecular weight solid acrylic polymer is also available from Schenectady International, Inc. under Product No. HRJ-10127. Tackifiers can also be added to the adhesive composition as is well known in the art.

The present adhesive composition is a hot melt adhesive. By hot melt adhesive, it is meant that the adhesive is essentially solventless or 100% solids and is processed in liquid form at elevated temperatures in the range of about 275° F. to 350° F. A preferred temperature range for compounding and coating the antimicrobial adhesive is 290° F. to 320° F. The antimicrobial containing adhesive is manufactured by heating the adhesive composition to about 250° F., including both a low molecular weight acrylic polymer and a medium molecular weight acrylic polymer along with any tackifiers to be utilized. The mixture is then heated to about 310° F. to about 315° F. and mixed until uniform with subsequent cooling to 290° F. to 295° F. at which point the diiodomethyl-p-tolylsulfone is added. The composition is mixed until uniform with subsequent packaging and cooling. The composition may then be hot melted and applied as needed by the user.

In a preferred application, the antimicrobial adhesive composition of the present invention is utilized to overly a polymeric substrate to form a surgical drape. The polymeric substrate is preferably a polyester or co-polyester sheet material which may have incorporated therein or coated on the side opposite the adhesive an antimicrobial agent.

These and various other advantages and features of novelty which characterize the present invention are pointed out with particularity in the claims annexed hereto and forming a part hereof. However, for a better understanding of the invention, its advantages, and the objects obtained by its use, reference should be made to the accompanying descriptive matter in which there are illustrated and described preferred embodiments of the present invention.

DETAILED DESCRIPTION OF THE PREFERRED EMBODIMENTS

Figure 1:
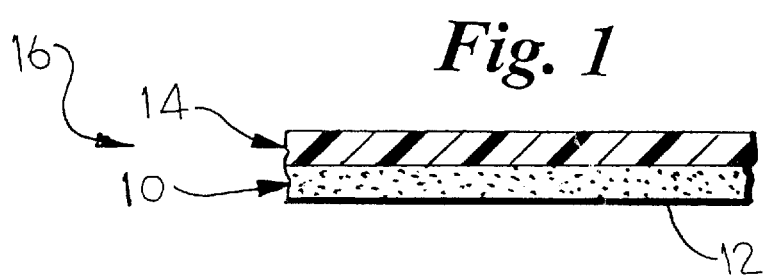
FIG. 1 is an enlarged fragmentary section of a surgical drape in accordance with the present invention.
Figure 2:
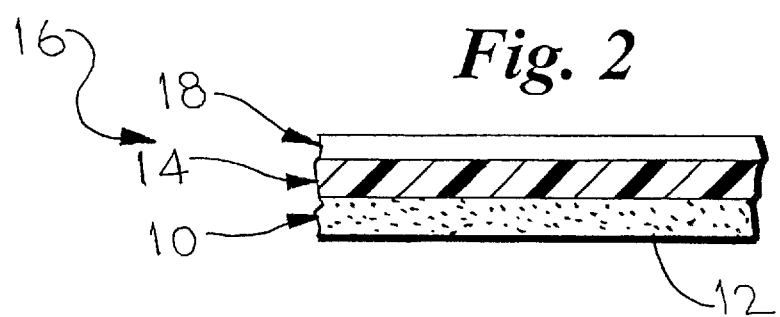
FIG. 2 is an alternate embodiment thereof.

As required, detailed embodiments of the present invention are disclosed herein. However, it is to be understood that the disclosed embodiments are merely exemplary of the present invention which may be embodied in various systems. Therefore, specific details disclosed herein are not to be interpreted as limiting, but rather as a basis for the claims and as a representative basis for teaching one skilled in the art to variously practice the present invention.

The present invention includes an adhesive compound which incorporates an adhesive component together with a broad spectrum antimicrobial agent dispersed therethrough. The antimicrobial agent is homogeneously dispersed throughout the adhesive layer 10. Active antimicrobial molecules of the present composition disassociate from the surface or leach out of the adhesive matrix over time, delivering biocidal activity at a distance from the adhesive surface 12. Applicants have conclusively demonstrated by zone of inhibition tests on a wide variety of infectious organisms the efficacy of the present composition. These tests showed that microbes were inhibited and killed at a distance from the sample as detailed in the attached experimental examples.

The adhesive of the present invention is specifically suited for use in skin contact applications during and after medical procedures, for example, as an adhesive in surgical drapes, wound dressings and tapes. The adhesive composition is a hot melt adhesive. By hot melt adhesive, it is meant that the adhesive is essentially solventless or 100% solids and flowable at elevated temperatures for application to a substrate material, such as a surgical drape 16. The preferred adhesive composition incorporates acrylic polymers and added tackifiers to form a pressure-sensitive adhesive which is particularly suited for use in surgical procedures.

A preferred combination of acrylic polymers to form the adhesive composition includes the combination of a low molecular weight solid acrylic polymer and a medium molecular weight solid acrylic polymer in a ratio of about 1 to 4, respectively, to optimize the adhesion of the adhesive to skin, cohesion and resistance to cold flow. A low molecular acrylic polymer is a polymer having a molecular weight ranging from about 90,000 to about 120,000, while a medium molecular weight acrylic polymer has a molecular weight ranging from about 140,000 to about 160,000. Suitable low molecular weight solid acrylic polymers and medium molecular weight solid acrylic polymers are available from Schenectady International, Inc. under Product Nos. HRJ-4326 and HRJ-10127, respectively.

The adhesive component of the composition can also include tackifiers as are well known in the art. Tackifiers contemplated include SYLVATEC, ZONAREZ and FORAL which are available from Arizona Chemical and Hercules, Inc.

As previously stated, the adhesive compound is a hot melt adhesive. A preferred composition has a feasible temperature range for working with the hot melt adhesive in the range of about 275° F. to 350° F. The preferred temperature range for compounding and coating with the adhesive is 290° F. to 320° F.

Applicants have found that the addition of a heat stable antimicrobial agent to the above adhesive composition results in an effective antimicrobial adhesive composition. In particular, Applicants have found that the addition of diiodomethyl-p-tolylsulfone to the above adhesive composition results in an effective antimicrobial adhesive which retains desirable properties during use and application at 275° F. to about 350° F. A preferred loading of antimicrobial agent to the adhesive is in the range of about 0.1% to about 2% by weight. A preferred loading is about 0.2% by weight to about 0.6% by weight of diiodomethyl-p-tolylsulfone to adhesive. The resulting heat stable antimicrobial containing adhesive is 100% solids and eliminates the need for use of a solvent and the requisite evaporation of such solvent. The hot melt adhesive can also be ethylene oxide sterilized under heat stress or radiation sterilized without loss of effectiveness of the antimicrobial.

A preferred source of diiodomethyl-p-tolylsulfone is AMICAL 48, available from Angus Chemical Company.

The antimicrobial containing adhesive composition of the present invention is manufactured by mixing thoroughly at elevated temperature the acrylic polymers and tackifiers. A temperature of about 250° F. to about 260° F. has been found to be adequate. Once mixed, the polymers and tackifiers are heated to 310° F. to 350° F. with continued mixing until uniform, followed by cooling to 290° F. to 295° F. The diiodomethyl-p-tolylsulfone is then added to the polymer and mixed until uniform. The resultant composition is packaged and cooled for subsequent hot melt applications.

In a preferred embodiment, the antimicrobial adhesive 10 is applied to, and overlies, a substrate layer 14 to form a surgical drape 16. The drape 16 can include an antimicrobial agent coating layer 18 applied to the substrate layer 14 on a side opposite that to which the adhesive 10 is applied.

As detailed below, the antimicrobial adhesive of the present invention was shown to be effective against a wide variety of microorganisms. The antimicrobial activity was determined by using a series of zone of inhibition tests, as are well known in the art. The effective release of antimicrobial from the adhesive is estimated from the measurement of a zone of inhibition (an area of inoculated plate where organisms do not grow) surrounding the sample.

The adhesive utilized for the tests included 2% diiodomethyl-p-tolylsulfone homogeneously dispersed as detailed above in an adhesive composition. The adhesive composition included 17% low molecular weight acrylic polymer (HRJ-4326 from Schenectady International, Inc.) and 67% medium molecular weight polymer (HRJ-10127 from Schenectady International, Inc.) along with 16% FLORAL 105 synthetic resin from Hercules, Inc. as a tackifier. The adhesive composition was prepared as detailed above. The adhesive composition was then melted and applied to a substrate layer 14 in a thin coating (approximately 0.05 mm in thickness). The substrate 14 was a co-polyester surgical drape material such as available from DuPont under the tradename HYTREL. The coated substrate 14 was cut to 6.0 mm disks for use in testing.

Adhesive coated disks were then exposed to microorganisms using the following procedure:

1. A microbial suspension containing=$1.0 \times 10^8$ organisms per ml in TSB was compared to the turbidity of a 0.5 MacFarland Standard.

2. A sterile swab was dipped into the culture suspension. The swab was rotated several times, pressing firmly on the inside wall of the tube above the fluid level. This removed excess inoculum from the swab.

3. The surface of a Mueller Hinton agar plate was inoculated by streaking the swab over the entire sterile agar surface. This streaking procedure was repeated two more times, rotating the plate approximately 60° each time to ensure an even distribution of inoculum.

4. The paper liner was removed from each 6 mm adhesive coated disc and the film was aseptically placed adhesive side down on the surface of the inoculated agar plate. Control samples were handled identically.

5. Immediately following the addition of the discs, the Mueller Hinton agar plates were placed in ambient air at 35°–37° for 18–24 hours. Following incubation, the zones of inhibition surrounding the discs were measured. When no zone was observed, the disc was aseptically removed and the area beneath the disc was evaluated for growth of the test organism. The tests were repeated two or three times, using relevant microorganisms. Experimental results are presented in the table below, reported as the average diameter zone of inhibition surrounding/under 6.0 mm samples. A 6.0 mm zone of inhibition indicates no growth of the test organism beneath the 6.0 mm test discs, while larger zones indicate effective antimicrobial activity at a distance from the disc.

TABLE 1

| Test Organism | Zone of Inhibition |
|---|---|
| *Staphylococcus aureus* (ATCC 6538) | 12.0 mm |
| *Escherichia coli* (ATCC 11229) | 6.0 mm |
| *Pseudomonas aeruginosa* (ATCC 15442) | 6.0 mm |
| *Klebsiella pneumoniae* (ATCC 4352) | 7.0 mm |
| *Pseudomonas cepacia* (ATCC 25416) | 6.0 mm |
| *Enterobacter cloacae* (ATCC 13047) | 6.0 mm |
| *Serratia marcescens* (ATCC 14746) | 6.5 mm |
| *Streptococcus pyogenes* (ATCC 19615) | 10.5 mm |
| *Enterococcus faecalis*-Vancomycin Resistant (ATCC 51299) | 9.5 mm |
| *Candida albicans* (ATCC 10231) | 33.5 mm |
| *Bacillus subtilis* (ATCC 19659) | 9.2 mm |

These results indicate that the present adhesive is effective in inhibiting these eleven relevant organisms, even after hot melt processing and ethylene oxide sterilization.

New characteristics and advantages of the invention covered by this document have been set forth in the foregoing description. It will be understood, however, that this disclosure is, in many respects, only illustrative. Changes may be made in details, particularly in matters of shape, size, and arrangement of parts, without exceeding the scope of the invention. The scope of the invention is, of course, defined in the language in which the appended claims are expressed.

What is claimed:

1. A hot melt adhesive composition having antimicrobial properties for skin contact applications comprising:
    a. an acrylic polymer; and
    b. an effective amount of diiodomethyl-p-tolylsulfone dispersed throughout said polymer;
    c. wherein said acrylic polymer comprises a mixture of a low molecular weight solid acrylic polymer and a medium molecular weight solid acrylic polymer.

2. The adhesive composition of claim 1, wherein said low molecular weight acrylic polymer has a molecular weight between about 90,000 and about 120,000 and said medium molecular weight acrylic polymer has a molecular weight between about 140,000 and about 160,000.

3. The adhesive composition of claim 1, wherein the ratio of low molecular weight polymer to medium molecular weight polymer is about 1 to 4.

4. The adhesive composition of claim 1, further comprising an effective amount of a tackifier.

5. A hot melt adhesive composition having antimicrobial properties for skin contact applications comprising:
    a. an acrylic polymer; and
    b. an effective amount of diiodomethyl-p-tolylsulfone dispersed throughout said polymer;
    c. wherein the concentration of diiodomethyl-p-tolylsulfone in said polymer composition is about 0.1% to about 2% by weight.

6. A hot melt adhesive composition having antimicrobial properties for skin contact applications comprising:
    a. an acrylic polymer; and
    b. an effective amount of diiodomethyl-p-tolylsulfone dispersed throughout said polymer;
    c. wherein said acrylic polymer has a melt temperature between about 275° F. and about 350° F.

7. A hot melt adhesive composition having antimicrobial properties comprising:
    a. an essentially 100% solids acrylic polymer for hot melt application; and
    b. an effective amount of diiodomethyl-p-tolylsulfone dispersed throughout said acrylic polymer;
    c. wherein said acrylic polymer comprises a mixture of a low molecular weight solid acrylic polymer and a medium molecular weight solid acrylic polymer.

8. The adhesive composition of claim 7, wherein said low molecular weight acrylic polymer has a molecular weight between about 90,000 and about 120,000 and said medium molecular weight acrylic polymer has a molecular weight between about 140,000 and about 160,000.

9. The adhesive composition of claim 8, wherein the ratio of low molecular weight polymer to medium molecular weight polymer is about 1 to 4.

10. The adhesive composition of claim 7, further comprising an effective amount of tackifier.

11. A hot melt adhesive composition having antimicrobial properties comprising:
    a. an essentially 100% solids acrylic polymer for hot melt application; and
    b. an effective amount of diiodomethyl-p-tolylsulfone dispersed throughout said acrylic polymer;
    c. wherein the concentration of diiodomethyl-p-tolylsulfone in said polymer composition is about 0.1% to about 2% by weight.

12. A hot melt adhesive composition having antimicrobial properties comprising:
    a. an essentially 100% solids acrylic polymer for hot melt application; and
    b. an effective amount of diiodomethyl-p-tolylsulfone dispersed throughout said acrylic polymer;
    c. wherein said acrylic polymer has a melt temperature between about 275° F. and about 350° F.

13. A surgical drape comprising:
    a. a sheet of polymeric substrate;
    b. a coating of an adhesive composition overlying said polymeric substrate wherein said adhesive composition is hot melt applied to said substrate and includes an acrylic polymer having an effective amount of diiodomethyl-p-tolylsulfone dispersed throughout said adhesive composition.

14. The surgical drape of claim 13 wherein said substrate comprises a sheet of co-polyester.

15. The surgical drape of claim 13, wherein said acrylic polymer comprises a mixture of a low molecular weight solid acrylic polymer and a medium molecular weight solid acrylic polymer.

16. The surgical drape of claim 15, wherein the ratio of low molecular weight polymer to medium molecular weight polymer is about 1 to 4.

17. The surgical drape of claim 13, wherein the concentration of diiodomethyl-p-tolylsulfone in said polymer composition is about 0.1% to about 2% by weight.

18. The surgical drape of claim 13, wherein said acrylic polymer has a melt temperature between about 275° F. and about 350° F.

19. The surgical drape of claim 13 further comprising an antimicrobial agent applied to said surgical drape on the side opposite said coating of an adhesive composition.

* * * * *